//  US006730796B2

United States Patent
Cheng et al.

(10) Patent No.: US 6,730,796 B2
(45) Date of Patent: May 4, 2004

(54) PROCESS FOR PREPARATION OF N-SUBSTITUTED 2-SULFANYLIMIDAZOLES

(75) Inventors: Jie Fei Cheng, Carlsbad, CA (US); Mi Chen, San Diego, CA (US)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/399,096

(22) PCT Filed: Oct. 12, 2001

(86) PCT No.: PCT/US01/42672

§ 371 (c)(1),
(2), (4) Date: Apr. 14, 2003

(87) PCT Pub. No.: WO02/32877

PCT Pub. Date: Apr. 25, 2002

(65) Prior Publication Data

US 2004/0039210 A1 Feb. 26, 2004

Related U.S. Application Data

(60) Provisional application No. 60/241,516, filed on Oct. 16, 2000.

(51) Int. Cl.$^7$ .............................................. C07D 233/84
(52) U.S. Cl. .................................................. 548/325.1
(58) Field of Search ....................................... 548/325.1

(56) References Cited

U.S. PATENT DOCUMENTS 4,160,841 A   7/1979  Heeres et al.

OTHER PUBLICATIONS

Elslager, E. F., et al., J. Heterocyclic Chem., Jan. 1980, pp. 129–136, vol. 17.
Hofmann, K., "The Chemistry of Heterocyclic Compounds", ed. by A. Weissberger, 1953, pp. 86–87, Interscience Publishers Inc., New York.
Uno, T., et al., Chem. Pharm. Bull., Oct. 1995, pp. 1724–1733, vol. 43, No. 10.
Yamada, M., et al., J. Med. Chem., 1996, pp. 596–604, vol. 39, No. 2.

*Primary Examiner*—Laura L. Stockton
(74) *Attorney, Agent, or Firm*—Daniel W. Collins

(57) ABSTRACT

This invention provides a process for preparing an N-substituted 2-sulfanylimidazole compound of the formula (I)

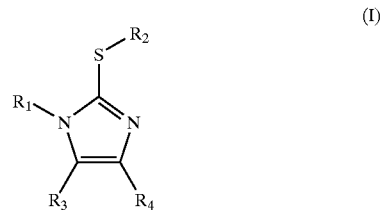

by reacting an isothiocyanate of the formula $R_1NCS$ with an α-aminocarbonyl compound of the formula $NH_2CHR_4C(OP)_2R_3$ and an alkyl halide or an activated aryl halide of the formula $R_2X$ in a solvent, alternatively, by reacting an isothiocyanate of the formula $R_1NCS$ with an α-aminocarbonyl compound of the formula $NH_2CHR_4C(OP)_2R_3$ before adding an alkyl halide of the formula $R_2X$, wherein $R_1$ and $R_2$ independently represent alkyl, heterocyclyl, aryl, or heteroaryl groups; $R_3$ and $R_4$ independently represent hydrogen, alkyl, heterocyclyl, aryl or heteroaryl or may form a non-aromatic ring; P represents a protecting group of a carbonyl group.

9 Claims, No Drawings

PROCESS FOR PREPARATION OF N-SUBSTITUTED 2-SULFANYLIMIDAZOLES

This application claims the benefit of Provisional application Ser. No. 60/241,516 filed Oct. 16, 2000.

FIELD OF INVENTION

This invention relates to a novel process for preparing N-substituted 2-sulfinylimidazoles compounds.

BACKGROUND

2-Sulfanylimidazoles are important heterocycles that are used in a number of pharmaceutical drugs or drug candidates. For example, both a GPIIB-IIIA antagonist OPC-29030 (*Chem. Pharm. Bull.* 43(10), 1724 (1995); CAS RNS: 161190-39-2) and an antiulcer agent T-330 (CSA RNS: 52410-51-2) which are in clinical trials contain an N-aryl 2-sulfanylimidazole substructure. On the other hand, a series of 4,5-unsubstituted 2-sulfanylimidazoles are described as potent inhibitors of the acid secretory enzyme $H^+/K^+$-ATPase (Yamada, M. et al.; *J. Med. Chem.* 39, 596 (1996)). These 2-sulfanylimidazoles are generally prepared from imidazole-2-thiones or imidazoles through alkylation with alkyl halides or activated aryl halides in the presence of bases. Either approach requires stepwise preparation and isolation of the respective intermediates. Furthermore, imidazole-2-thiones are typically synthesized from a thiourea acetal intermediate via an acid-catalyzed cyclization (Hofmann, K. in "*The Chemistry of Heterocyclic Compounds*", eds. By A. Weissberger, Interscience Publishers Inc., New York, 1953, p86–87; Elslager, E. F. et al., *J. Heterocyclic Chem.* 17, 129 (1980)). The reactions mentioned above were conducted under either strongly acidic or basic conditions which are incompatible with many functional groups.

SUMMARY OF THE INVENTION

The inventors have developed a convenient one step synthesis of N-substituted 2-sulfanylimidazole compounds without using a base or an acid, thus allowing for functional groups that would otherwise be incompatible with such a reaction.

This invention relates to a process for preparing an N-substituted 2-sulfanylimidazole compound of the formula (I)

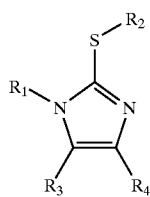

(I)

by reacting an isothiocyanate of the formula $R_1NCS$ with an α-aminocarbonyl compound of the formula $NH_2CHR_4C(OP)_2R_3$ and an alkyl halide or an activated aryl halide of the formula $R_2X$ in a solvent, alternatively, by reacting an isothiocyanate of the formula $R_1NCS$ with an α-aminocarbonyl compound of the formula $NH_2CHR_4C(OP)_2R_3$ before adding an alkyl halide or an activated aryl halide of the formula $R_2X$, wherein $R_1$ and $R_2$ independently represent alkyl, heterocyclyl, aryl, or heteroaryl groups; $R_3$ and $R_4$ independently represent hydrogen, alkyl, heterocyclyl, aryl or heteroaryl or may form a non-aromatic ring; P represents a protecting group of a carbonyl group.

Preferably, $R_1$ represents aryl or heteroaryl. Preferably, $R_2$ represents alkyl. Preferably, $R_3$ represents hydrogen. Preferably, $R_4$ represents hydrogen. Preferably, said halide is chloride, bromide or iodide. Preferably, the protecting group of the carbonyl group of α-aminocarbonyl is dialkyl or cyclic alkyl acetal.

This invention relates to a convenient one step synthesis of N-substituted 2-sulfanylimidazole from an isothiocyanate, an α-aminocarbonyl compound and an alkyl halide or an activated aryl halide. Reaction of an isothiocyanate with an α-aminocarbonyl compound affords a thiourea acetal intermediate, which without isolation or purification provides the desired N-substituted 2-sulfanylimidazole upon treatment with an alkyl halide.

DETAILED DESCRIPTION OF THE INVENTION

The detailed description of the invention which follows is not intended to be exhaustive or to limit the invention to the precise details or examples disclosed. Details and examples have been chosen to explain the invention to others skilled in the art.

The processes of this invention described herein and in the claims, may be performed in s veral ways. Preferred methodologies are described as follows.

This invention provides a process for preparing an N-substituted 2-sulfanylimidazole compound of the formula (I)

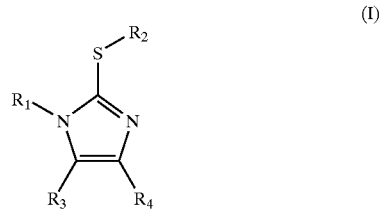

(I)

by reacting an isothiocyanate of the formula $R_1NCS$ with an α-aminocarbonyl compound of the formula $NH_2CHR_4C(OP)_2R_3$ and an alkyl halide or an activated aryl halide of the formula $R_2X$ in a solvent, alternatively, by reacting an isothiocyanate of the formula $R_1NCS$ with an α-aminocarbonyl compound of the formula $NH_2CHR_4C(OP)_2R_3$ before adding an alkyl halide of the formula $R_2X$, wherein $R_1$ and $R_2$ independently represent alkyl, heterocyclyl, aryl, or heteroaryl groups; $R_3$ and $R_4$ independently represent hydrogen, alkyl, heterocyclyl, aryl or heteroaryl or may form a non-aromatic ring; P represents a protecting group of a carbonyl group.

Preferably, $R_1$ represents aryl or heteroaryl. Preferably, $R_2$ represents alkyl. Preferably, $R_3$ represents hydrogen. Preferably, $R_4$ represents hydrogen. Preferably, said halide is chloride, bromide or iodide. Preferably, the protecting group of the carbonyl group of α-aminocarbonyl is dialkyl or cyclic alkyl acetal.

The reaction is performed by mixing all reactants, i.e., an isothiocyanate of the formula $R_1NCS$, an α-aminocarbonyl compound of the formula $NH_2CHR_4C(OP)_2R_3$ and an alkyl halide of the formula $R_2X$ in a solvent. Alternatively, an isothiocyanate of the formula $R_1NCS$ is reacted with a protected α-aminocarbonyl compound of the formula $NH_2CHR_4C(OP)_2R_3$ in a solvent to provide a thiourea intermediate. There is no restriction on the solvent used in this reaction. The reaction can be conducted in either organic or inorganic solvents. Preferably, the solvents used in the invention are organic solvents. More preferably, the reaction is conducted in an organic solvent, such as toluene or ethanol. Subsequently, the thiourea intermediate is reacted with an alkyl halide to provide the desired N-substituted 2-sulfanylimidazole compound. Preferably, the reaction is conducted under sealed condition. Preferably, alcohol solvent is added along with an alkyl halide or an activated aryl halide. Preferably, the reaction is conducted at elevated temperature aftermixing all reactants. More preferably, the reaction is heated to 60–80° C. from room temperature. The reaction is useful for a large scale production of N-substituted 2-sulfanylimidazoles. This invention is useful for preparing important pharmaceutical agents such as drugs or drug candidates which contain N-substituted 2-sulfanylimidazoles.

DEFINITION

As used above, and throughout the description of the invention, the following terms, unless otherwise indicated, shall be understood to have the following meanings:

"Activated aryl halide", as used herein, means an aryl halide that is substituted by some type of substituents that activate the aryl halide so that it can be reacted with thiourea intermediate to form the desired N-substituted 2-sulfanylimidazole. Substituents used for activation of an aryl halide are electron-withdrawing groups.

"Alkyl", as used herein, means a cyclic, branched, or straight chain chemical group containing only carbon and hydrogen, such as methyl, pentyl, and adamantyl. Alkyl groups can either be unsubstituted or substituted with one or more substituents, e.g., halogen, alkoxy, acyloxy, amino, cyano, nitro, hydroxyl, mercapto, carboxy, benzyloxy, aryl, heteroaryl, or other functionality that may be suitably blocked, if necessary for purposes of the invention, with a protecting group. Alkyl groups can be saturated or unsaturated (e.g., containing —C=C— or —C≡C— subunits), at one or several positions. Typically, alkyl groups will comprise 1 to 12 carbon atoms, preferably 1 to 10, and more preferably 1 to 8 carbon atoms.

"Aryl", as used herein, means a monovalent unsaturated aromatic carbocyclic group having a single-ring (e.g., phenyl) or multiple condensed rings (e.g., naphthyl or anthryl), which can be optionally unsubstituted or substituted with amino, cyano, hydroxyl, lower alkyl, haloalkyl, alkoxy, nitro, halo, mercapto, and other substituents.

"Electron-withdrawing group", as used herein, means a specific group that makes the electron density of the parent molecule unevenly distributed when it is attached to the parent molecule. An electron-withdrawing group pulls the electron from the parent molecule toward this group. An electron-withdrawing group includes but not limited to a nitro, cyano or trifluoromethyl group. More examples of electron-withdrawing groups can be found in March, *Advanced Organic Chemistry*, $4^{th}$, Wiley Interscience, 1992.

"Elevated temperature", as used herein, means the reaction is conducted at a temperature that is higher than room temperature. The reaction in the invention is conducted at a temperature ranging from 60 to 80° C. after all the reactants are added.

"Halo", as used herein, means chloro, bromo or iodo atoms in the invention. The fluorine atom is excluded in the invention. A compound containing halo atom is referred as a halide.

"Heteroaryl", as used herein, means a monovalent unsaturated aromatic carbocyclic group having a single ring (e.g., pyrridyl or furyl) or multiple condensed rings (e.g., indolizinyl or benzothienyl) and having at least one hetero atom, such as N, O, or S, within the ring, which can optionally be unsubstituted or substituted with amino, cyano, nitro, hydroxyl, alkyl, haloalkyl, alkoxy, aryl, halo, mercapto, and other substituents.

"Heterocyclyl", as used herein, means radical heterocycles which are saturated, or unsaturated and non-aromatic. These may be substituted or unsubstituted, and are attached to the core structure via any available valence, preferably any available carbon. More preferred heterocycles are of 5 or 6 members. In six membered non-aromatic monocyclic heterocycles, the heteroatom(s) are from one to three Ns, and wherein when the heterocycle is five membered and non-aromatic, preferably it has one or two heteroatoms selected from O, N, or S.

"Large scale", as used herein, means that the reaction provides the desired product in an industrial scale or in a large quantity. The reaction in the invention can be used either to produce a picogram, milligram, or gram quantity or to produce on the kilogram or tons scale.

"Protecting group", as used herein, means a chemical group that exhibits the following characteristics: 1) reacts selectively with the desired functionality in good yield to give a protected substrate that is stable to the projected reactions for which protection is desired; 2) is selectively removable from the protected substrate to yield the desired functionality; and 3) is removable in good yield by reagents compatible with the other functional group(s) generated in such protected reactions. Most wildly used protecting group for a carbonyl functionality is acetal (or ketal). Examples of more protecting groups can be found in Greene and Wuts, *Protective Groups in Organic Synthesis*, $2^{nd}$ Ed. John Wiley & Sons, (1991).

"Sealed condition", as herein used, means that the reaction is conducted in a container that is not exposed to air directly. Any isolated system that is not exposed directly to air is a sealed system. For example, the reactions performed in a sealed tube or in a capped container or under argon or other inert gas atmosphere are considered to be under sealed condition.

"Solvent", as herein used, means a liquid that can dissolve another compound and has no adverse effect on the reaction or on the reagents involved. Examples of suitable solvents include alcohols (methanol, 1-butanol, phenol, trifluoroethanol, hexafluoro-2-propanol, etc.), hydrocarbons (benzene, toluene, etc.), amides (dimethyl acetamide, dimethylformamide, etc.), halides (dichloroethane, dichloroiethane, etc.), and ethers (tetrahydrofuran, dioxane, etc.). Other solvents include water, 1-methyl-2-pyrrolidine, diethyl phosphite, tetramethaylsulphone, dimethyl sulphoxide, acetonitrile and pyridine.

The following abbreviations have the indicated meanings:
Bn=benzyl
$CDCl_3$=deutered chloroform
$CH_2Cl_2$=dichloromethane
ESIMS=electron spray mass spectrometry
EtOAc=ethyl acetate
EtOH=ethanol
Ph=phenyl
TLC=thin layer chromatography
Me=methyl
Et=ethyl
n-Bu=normal butyl
t-Bu=tertiary butyl

EXAMPLES

To further illustrate this invention, the following examples are included. The examples should not, of course, be construed as specifically limiting the invention. Variations of these examples within the scope of the claims are within the purview of one skilled in the art are considered to fall within the scope of the invention as described, and claimed herein. The reader will recognize that the skilled artisan, armed with the present disclosure, and skill in the art is able to prepare and use the invention without exhaustive examples.

Trademarks used herein are examples only and reflect illustrative materials used at the time of the invention. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the invention.

$^1$H nuclear magnetic resonance spectra (NMR) is measured in $CDCl_3$ or other solvents as indicated by a Varian NMR spectrometer (Unity Plus 400, 400 MHz for $^1$H) unless otherwise indicated and peak positions are expressed in parts per million (ppm) downfield from tetramethylsilane. The peak shapes are denoted as follows, s, singlet; d, doublet; t, triplet; m, multiplet.

Example 1
General Procedure for the Synthesis of N-substituted 2-Sulfanylimidazoles (1)

Isothiocyanate (1 mmol) and α-aminocarbonyl compound (1 mmol) were mixed together in toluene or ethanol (2 mL). The reaction mixture was allowed to stir at room temperature under argon until the reaction is completed as evidenced by TLC. After addition of a halide (1.5 mmol) in EtOH (2 mL), the reaction mixture was heated to 80° C. for 14 hrs under sealed condition. The solvent was removed under reduced pressure and the resulting residue was purified by a preparative TLC with 5% acetone in $CH_2Cl_2$ to afford the desired N-substituted 2-sulfanylimidazole.

Example 2
General Procedure for the Synthesis of N-substituted 2-Sulfanylimidazoles (2)

Isothiocyanate (1 mmol), α-aminocarbonyl compound (1 mmol) and a halide (1.5 mmol) in EtOH (2 mL) are mixed together in toluene or ethanol (2 mL) at the room temperature under argon atmosphere. The reaction mixture is heated to 80° C. for 14 hrs under sealed condition. The solvent is removed under reduced pressure and the resulting residue is purified by a preparative TLC with 5% acetone in $CH_2Cl_2$ to afford the desired N-substituted 2-sulfanylimidazole.

Example 3
Preparation of Give N-(p-methoxyphenyl)-2-benzylthioimidazole p-Methoxyphenylisocyanate (1 mmol) and aminoacetaldehyde diethyl acetal (1 mmol) were mixed together in toluene (2 mL). The reaction mixture was allowed to stir at room temperature under argon until the reaction is completed as evidenced by TLC. After addition of benzyl bromide (1.5 mmol) in EtOH (2 mL), the reaction mixture was heated to 80° C. for 14 hrs. Following removal of the solvent, the residue was purified by preparative TLC with 5% acetone in dichloromethane to give N-(p-methoxyphenyl)-2-benzylthioimidazole in 92.1% yield. $^1$H NMR ($CDCl_3$) δ7.2 (brs, 6H), 7.0 (m, 3H), 6.8 2 (m, 2H), 4.21 (s, 2H), 3.78 (s, 3H). ESIMS: m/z 297 (M+H), $C_{17}H_{16}N_2OS$.

Example 4

The following compounds are also exemplified in this invention.

| No. | $R_1$ | $R_2$ | $R_3$ | $R_4$ |
|---|---|---|---|---|
| 1 | Ph | p-tBu-Bn | H | H |
| 2 | Ph | m-MeOBn | H | H |
| 3 | p-MeOPh | Bn | H | H |
| 4 | Ph | Allyl | H | H |
| 5 | Ph | p-$NO_2$Bn | H | H |
| 6 | Ph | Cyclohexylmethyl | H | H |
| 7 | Ph | o-Methylpropyl | H | H |
| 8 | Ph | Me | H | p-MeOPh |
| 9 | Ph | Me | Me | H |
| 10 | p-$CF_3$Ph | Bn | —$CH_2CH_2CH_2$— | |

We claim:

1. A process for preparing an N-substituted 2-sulfanylimidazole compound of the formula

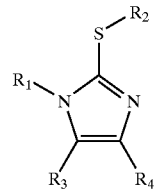

by reacting an isothiocyanate of the formula $R_1NCS$ with an α-aminocarbonyl compound of the formula $NH_2CHR_4C(OP)_2R_3$ and an alkyl halide or an activated aryl halide of the formula $R_2X$ in a solvent, wherein $R_1$ and $R_2$ independently represent alkyl, heterocyclyl, aryl, or heteroaryl groups; $R_3$ and $R_4$ independently represent hydrogen, alkyl, heterocyclyl, aryl or heteroaryl or may form a non-aromatic ring; P represents a protecting group of a carbonyl group and wherein X is a halide.

2. The process of claim 1, wherein $R_1$ represents aryl or heteroaryl.

3. The process of claim 1, wherein $R_2$ represents alkyl.

4. The process of claim 1, wherein $R_3$ represents hydrogen.

5. The process of claim 1, wherein $R_4$ represents hydrogen.

6. The process of claim 1, wherein said halide is added after mixing said isocyanate and said α-aminocarbonyl compound.

7. The process of claim 1, wherein the reaction is conducted under a sealed condition.

8. The process of claim 1, wherein the reaction is conducted in a large scale.

9. The process of claim 1, wherein the reaction is conducted at a elevated temperature.

* * * * *